(12) United States Patent
Lee et al.

(10) Patent No.: US 10,458,943 B2
(45) Date of Patent: Oct. 29, 2019

(54) IONIC CONDUCTIVITY MEASUREMENT DEVICE OF ELECTROLYTE MEMBRANE

(71) Applicant: KOREA INSTITUTE OF SCIENCE AND TECHNOLOGY, Seoul (KR)

(72) Inventors: So Young Lee, Seoul (KR); Hyoung-Juhn Kim, Seoul (KR); Young Seung Na, Seoul (KR); Jin Young Kim, Seoul (KR); Sung Jong Yoo, Seoul (KR); Jong Hyun Jang, Seoul (KR); Jonghee Han, Seoul (KR); Suk Woo Nam, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 190 days.

(21) Appl. No.: 15/861,998

(22) Filed: Jan. 4, 2018

(65) Prior Publication Data

US 2018/0202970 A1 Jul. 19, 2018

(30) Foreign Application Priority Data

Jan. 17, 2017 (KR) ........................ 10-2017-0007970

(51) Int. Cl.
*G01N 27/62* (2006.01)
*G01K 13/00* (2006.01)
(Continued)

(52) U.S. Cl.
CPC ............. *G01N 27/62* (2013.01); *G01K 13/00* (2013.01); *G01R 27/26* (2013.01);
(Continued)

(58) Field of Classification Search
CPC ...... G01N 27/62; G01N 27/041; G01R 27/26; G01K 13/00; H01M 8/1067; H01M 8/0254; H01M 8/0258; H01M 8/0247
See application file for complete search history.

(56) References Cited

U.S. PATENT DOCUMENTS

| 2002/0071981 A1* | 6/2002 | Sano | H01M 8/04291 |
| | | | 429/413 |
| 2013/0076379 A1* | 3/2013 | Dileo | H01M 8/04313 |
| | | | 324/699 |

FOREIGN PATENT DOCUMENTS

| KR | 20-0288338 Y1 | 9/2002 |
| KR | 10-2008-0004976 A | 1/2008 |

(Continued)

*Primary Examiner* — Ula C Ruddock
*Assistant Examiner* — Matthew W Van Oudenaren
(74) *Attorney, Agent, or Firm* — Rabin & Berdo, P.C.

(57) ABSTRACT

An ionic conductivity measurement device of an electrolytic membrane includes a humidification chamber configured to accommodate an ion-conductive electrolytic membrane and having concave grooves respectively formed at both sides thereof which face the electrolytic membrane to form a measurement space for measuring ionic conductivity of the electrolytic membrane; a plurality of channels formed at a bottom surface of each of the concave grooves; a gas distribution unit detachably coupled to each of the concave grooves with the electrolytic membrane being interposed therebetween; and a plurality of electrodes provided in contact with one side of the electrolytic membrane and supported by the gas distribution unit, the plurality of electrodes being disposed side by side to measure an impedance of the electrolytic membrane.

11 Claims, 5 Drawing Sheets

(51) Int. Cl.
*G01R 27/26* (2006.01)
*H01M 8/0247* (2016.01)
*H01M 8/0258* (2016.01)
*H01M 8/1067* (2016.01)

(52) U.S. Cl.
CPC ........ *H01M 8/0247* (2013.01); *H01M 8/0258* (2013.01); *H01M 8/1067* (2013.01)

(56) References Cited

FOREIGN PATENT DOCUMENTS

KR 10-2008-0065375 A 7/2008
KR 10-2010-0041748 A 4/2010

* cited by examiner

IONIC CONDUCTIVITY MEASUREMENT DEVICE OF ELECTROLYTE MEMBRANE

CROSS-REFERENCE TO RELATED APPLICATIONS

This application claims, under 35 U.S.C. § 119, the priority of Korean Patent Application No. 10-2017-0007970 filed on Jan. 17, 2017 in the Korean Intellectual Property Office, the disclosure of which is incorporated herein by reference in its entirety.

TECHNICAL FIELD

The present disclosure relates to an ionic conductivity measurement device of an electrolytic membrane, and more particularly to an ionic conductivity measurement device of an electrolytic membrane, which may measure ionic conductivity of a high-molecular electrolytic membrane at specific temperature and humidity.

BACKGROUND

A fuel cell includes an anode for supplying hydrogen ions and electrons from hydrogen, and a cathode capable of supplying oxygen.

Seeing the principle of generating electricity in a fuel cell, if fuel is supplied to the anode, the fuel is ionized to generate hydrogen ions and electrons. Also, the hydrogen ion penetrates an electrolytic membrane to reach the cathode and combines with oxygen to become water. The electrons produced at the anode generate an electric current at an electric load connected between the anode and the cathode, reach the cathode, and react with the hydrogen ions and oxygen to generate water vapor.

The fuel cell is classified into a polymer electrolyte membrane fuel cell (PEMFC), a direct methanol fuel cell (DMFC), a direct borohydride fuel cell (DBFC), a solid alkaline fuel cell (SAFC) and the like.

Among the above fuel cells, the polymer electrolyte membrane fuel cell, the direct methanol fuel cell and the direct borohydride fuel cell employ a cation exchange membrane, which is a cation-conducting or hydrogen ion-conducting electrolytic membrane, as an electrolyte. Also, the solid alkaline fuel cell and the direct borohydride fuel cell employ an anion exchange membrane, which is a hydroxide ion-conducting electrolyte membrane. Here, the direct borohydride fuel cell may use both the cation exchange membrane and the anion exchange membrane.

The electrolytic membrane with ionic conductivity used in the fuel cell is an important factor for determining the efficiency and characteristics of the fuel cell, and the electrolytic membrane should have high hydrogen ion conductivity.

In addition, if hydrogen ion conductivity is irregular depending on the location of the electrolytic membrane, the current may not flow uniformly and may give adverse effects on the durability and performance of the electrolytic membrane. Thus, the electrolytic membrane should have uniform hydrogen ion conductivity over the entire region.

Therefore, it is necessary to investigate the hydrogen ion conductivity of the electrolytic membrane more precisely and miniaturize the equipment for measuring ionic conductivity of the electrolytic membrane.

RELATED LITERATURES

Patent Literature

[Patent Literature 1] Korean Utility Model Registration No. 20-0288338 (issued on Sep. 11, 2002)

SUMMARY

The present disclosure is directed to providing a miniaturized ionic conductivity measurement device of an electrolytic membrane, which may accurately measure the hydrogen ion conductivity of an electrolytic membrane under specific temperature and humidity conditions.

In one aspect, there is provided an ionic conductivity measurement device of an electrolytic membrane, comprising: a humidification chamber configured to accommodate an ion-conductive electrolytic membrane and having concave grooves respectively formed at both sides thereof which face the electrolytic membrane to form a measurement space for measuring ionic conductivity of the electrolytic membrane, the humidification chamber having a first humid gas inlet and a first humid gas outlet formed through the concave groove; a plurality of channels formed at a bottom surface of each of the concave grooves so that the first humid gas inlet and the first humid gas outlet are connected to communicate with each other, the plurality of channels having an open top; a gas distribution unit detachably coupled to each of the concave grooves with the electrolytic membrane being interposed therebetween, the gas distribution unit being closely adhered to a top portion of the plurality of channels and uniformly distributing the humid gas moving along the plurality of channels toward the electrolytic membrane; and a plurality of electrodes provided in contact with one side of the electrolytic membrane and supported by the gas distribution unit, the plurality of electrodes being disposed side by side to measure an impedance of the electrolytic membrane.

The first humid gas inlet and the first humid gas outlet may be formed at edges of the concave grooves oppositely, and the plurality of channels may be formed at the bottom surface of the concave groove in a concavely depressed form with an open top and are arranged side by side.

The plurality of channels may be disposed at the bottom surface of the concave groove side by side in a zigzag form.

The gas distribution unit may include a gas distribution plate inserted into the concave groove and closely adhered to the top of the plurality of channels and having a plurality of gas distribution holes communicating with the plurality of channels.

The gas distribution hole may be formed to have a diameter greater than a width of the channel.

The humidification chamber may include a pair of chamber blocks so that the concave groove is formed at one surface thereof which faces the electrolytic membrane, the pair of chamber blocks are coupled to be closely adhered to each other to form the measurement space, and the first humid gas inlet and the first humid gas outlet are formed in the pair of chamber blocks through the concave groove.

The ionic conductivity measurement device may further include a temperature sensor inserted into one side of the chamber block to measure temperature of the measurement space.

The ionic conductivity measurement device may further include a sealing member disposed to surround an outer side of the concave groove to seal the pair of chamber blocks to each other when the pair of chamber blocks are coupled to be closely adhered to each other.

The ionic conductivity measurement device may further include a temperature adjustment unit installed at the humidification chamber to adjust internal temperature of the measurement space.

The humidification chamber may further include a pair of end blocks respectively coupled to outer sides of the pair of chamber blocks and having a second humid gas inlet and a second humid gas outlet formed to communicate with the first humid gas inlet and the first humid gas outlet, respectively, and the temperature adjustment unit may include a heat bar inserted into one side of the end block to adjust internal temperature of the measurement space.

The chamber block and the gas distribution unit may be made of any one of polyetherether ketone (PEEK) and polytetrafluoro ethylene (PTFE).

In an embodiment of the present disclosure, since humid gas is supplied to and discharged from a miniaturized humidification chamber, it is possible to prevent water from condensing and accumulating in the humidification chamber when measuring the ionic conductivity of the electrolytic membrane.

In addition, in an embodiment of the present disclosure, it is possible to measure the ionic conductivity over the entire region of the electrolytic membrane while changing the temperature in the humidification chamber and the humidity of the humid gas.

DETAILED DESCRIPTION OF EMBODIMENTS

In order to fully understand the operational advantages of the present disclosure and the object achieved by the implementation of the present disclosure, the accompanying drawings illustrating embodiments of the present disclosure and the contents disclosed in the accompanying drawings should be referred to.

Hereinafter, the present disclosure will be described in detail by explaining embodiments of the present disclosure with reference to the accompanying drawings. Like reference signs in the drawings denote like elements.

Figure 1:
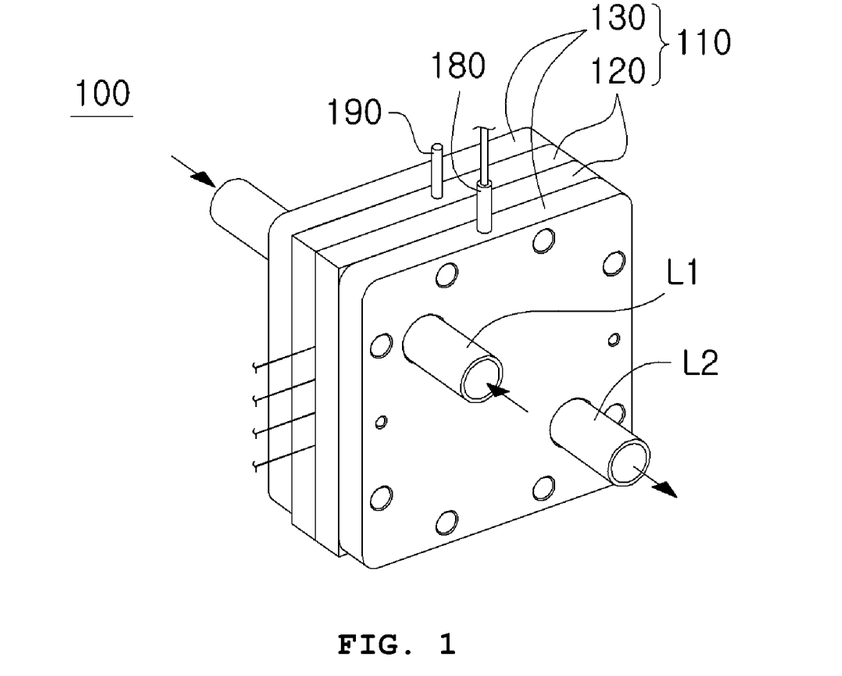
FIG. 1 is a perspective view showing an ionic conductivity measurement device of an electrolytic membrane according to an embodiment of the present disclosure.
Figure 2:
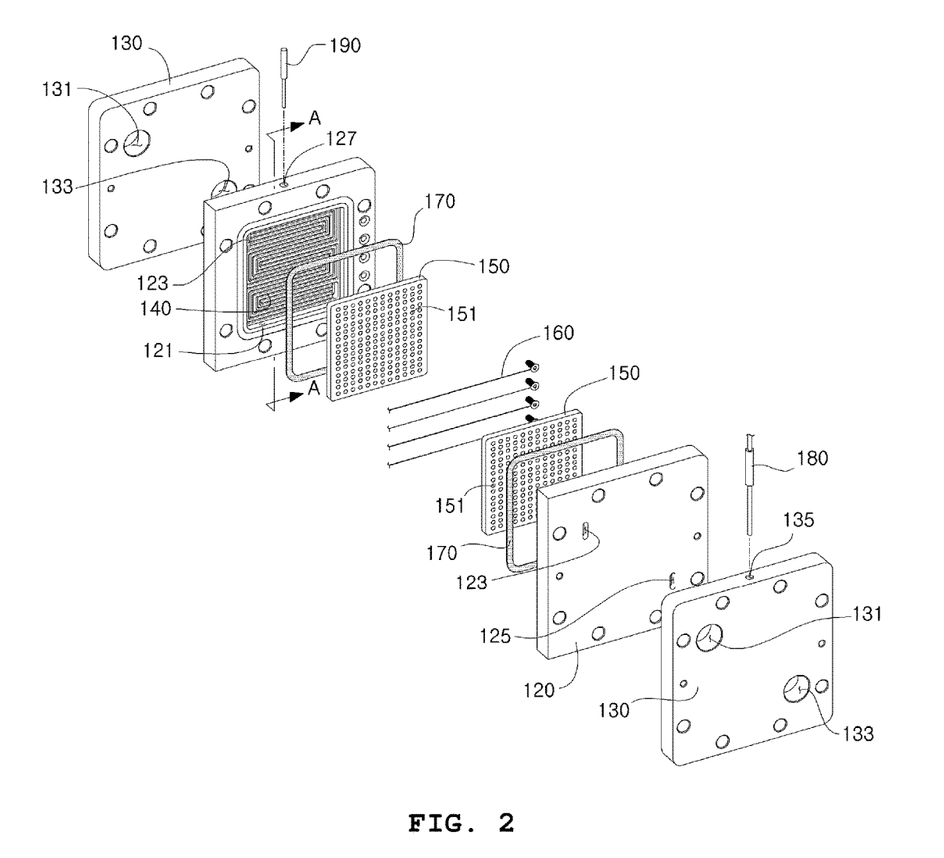
FIG. 2 is an exploded perspective view showing the ionic conductivity measurement device of an electrolytic membrane according to an embodiment of the present disclosure.
Figure 3:
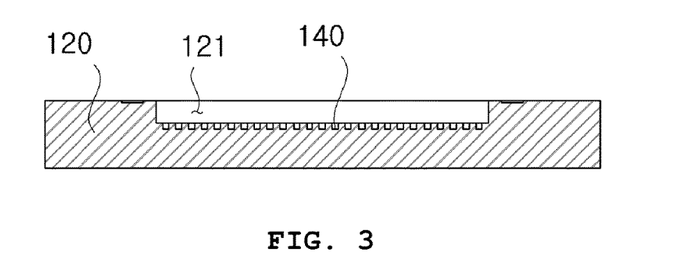
FIG. 3 is a cross-sectioned view, taken along the line A-A of FIG. 2, showing a chamber block according to an embodiment of the present disclosure.
Figure 4:
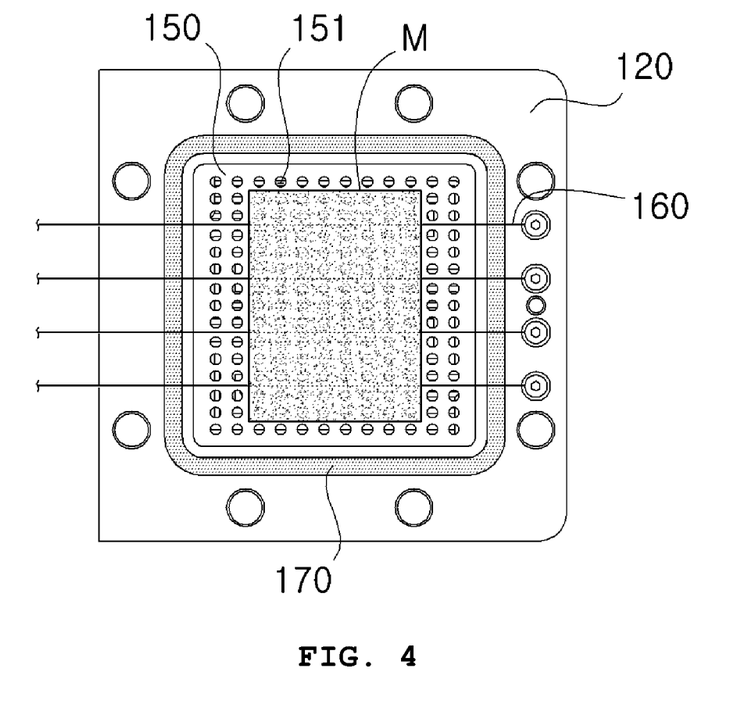
FIG. 4 is a diagram showing that an electrolytic membrane is disposed at the ionic conductivity measurement device of an electrolytic membrane according to an embodiment of the present disclosure.
Figure 5:
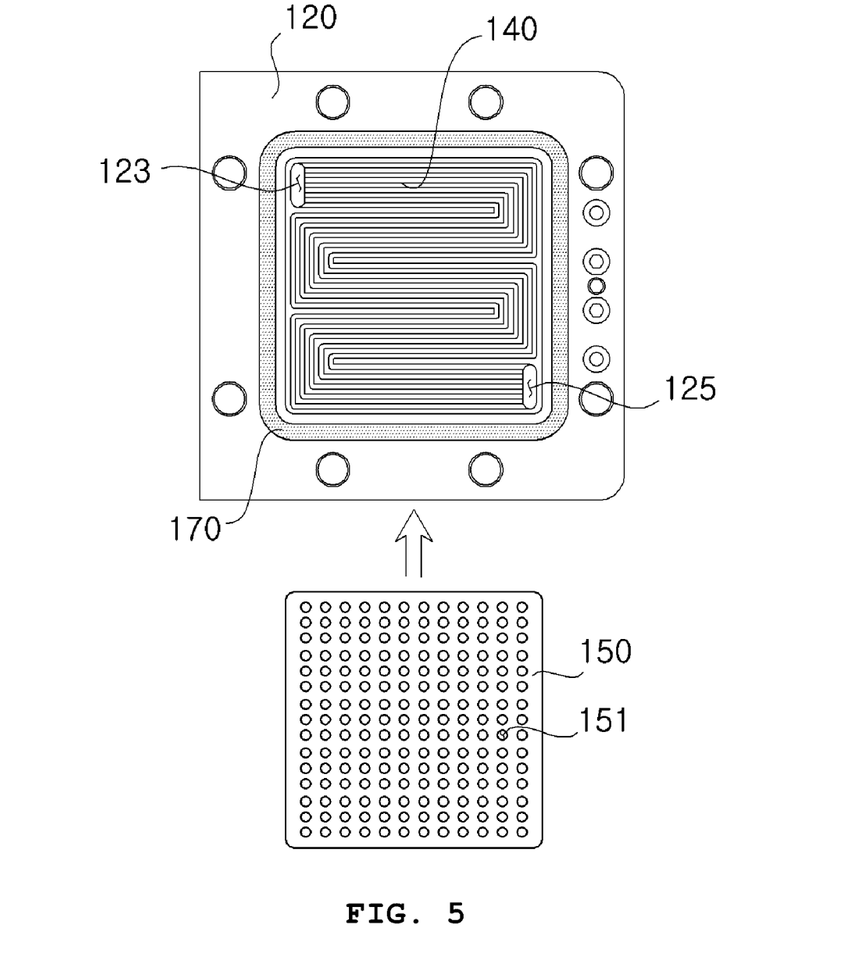
FIG. 5 is a side view showing a chamber block and a gas distribution plate according to an embodiment of the present disclosure.
Figure 6:
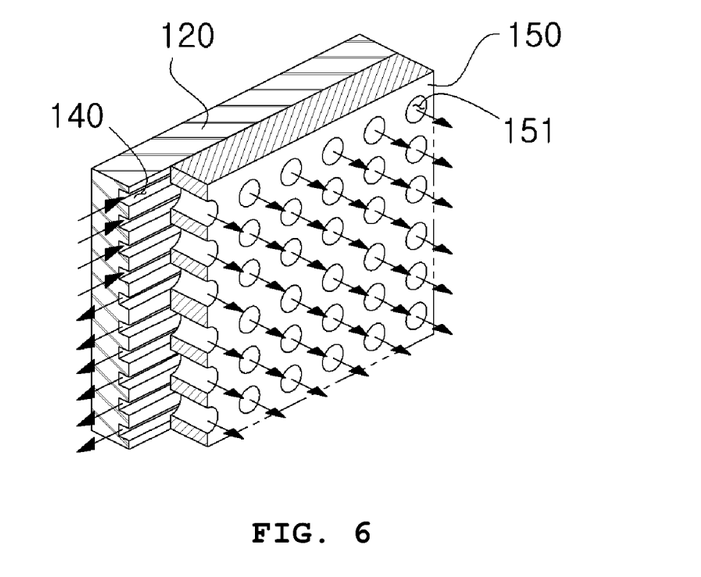
FIG. 6 is a cross-sectioned view showing that a humid gas is discharged through a gas distribution plate according to an embodiment of the present disclosure.

FIG. 1 is a perspective view showing an ionic conductivity measurement device of an electrolytic membrane according to an embodiment of the present disclosure, FIG. 2 is an exploded perspective view showing the ionic conductivity measurement device of an electrolytic membrane according to an embodiment of the present disclosure, FIG. 3 is a cross-sectioned view, taken along the line A-A of FIG. 2, showing a chamber block according to an embodiment of the present disclosure, FIG. 4 is a diagram showing that an electrolytic membrane is disposed at the ionic conductivity measurement device of an electrolytic membrane according to an embodiment of the present disclosure, FIG. 5 is a side view showing a chamber block and a gas distribution plate according to an embodiment of the present disclosure, and FIG. 6 is a cross-sectioned view showing that a humid gas is discharged through a gas distribution plate according to an embodiment of the present disclosure.

Referring to FIGS. 1 to 4, an ionic conductivity measurement device 100 of an electrolytic membrane according to an embodiment of the present disclosure includes a humidification chamber 110 configured to accommodate an ion-conductive electrolytic membrane M so that a humid gas flows in and out, a channel 140 formed at a bottom surface of a concave groove 121 formed in the humidification chamber 110 so that the humid gas flows therethrough, a gas distribution unit 150 detachably coupled to the concave groove 121 formed in the humidification chamber 110 to uniformly distribute the humid gas toward the electrolytic membrane M, and a plurality of electrodes 160 provided inside the humidification chamber 110 in contact with one surface of the electrolytic membrane M to measure an impedance of the electrolytic membrane M.

Meanwhile, in this embodiment, the humid gas includes hydrogen, oxygen, air or the like and is supplied to the ionic conductivity measurement device 100 of an electrolytic membrane according to this embodiment in a state where temperature and humidity are controlled.

The humidification chamber 110 of this embodiment serves to provide a measurement space for measuring the ionic conductivity of the electrolytic membrane M.

In order to miniaturize the ionic conductivity measurement device 100 of an electrolytic membrane, the size of the humidification chamber 110 accommodating the electrolytic membrane M should be reduced. Accordingly, in order to form the measurement space for measuring the ionic conductivity of the electrolytic membrane M, concave grooves 121 are formed at both sides, which face the electrolytic membrane M accommodated in the humidification chamber 110, respectively.

The humidification chamber 110 of this embodiment may have an integrated housing structure where the electrolytic membrane M may enter and exit, and as shown in FIGS. 1 and 2, a pair of chamber blocks 120 may be coupled to each other so that the electrolytic membrane M may be easily accommodated in the humidification chamber 110.

Referring to FIGS. 1 to 4, the humidification chamber 110 will be described below.

The humidification chamber 110 includes a pair of chamber blocks 120 which are disposed to face each other and coupled to be closely adhered to each other so that the electrolytic membrane M is interposed therebetween.

A concave groove 121 is formed at one side of each chamber block 120, which faces the electrolytic membrane M accommodated in the chamber block 120. Thus, if the pair of chamber blocks 120 are closely adhered to each other, a measurement space for measuring the ionic conductivity of the electrolytic membrane M is formed between the concave grooves 121.

In addition, a first humid gas inlet 123 for supplying a humid gas and a first humid gas outlet 125 for discharging the supplied humid gas are formed at each chamber block 120. Since the first humid gas inlet 123 and the first humid gas outlet 125 are formed in each chamber block 120 as described above, the humid gas is supplied and discharged at both sides of the electrolytic membrane M.

As shown in FIG. 5, the first humid gas inlet 123 is formed at an upper left edge and the first humid gas outlet 125 is formed at a lower right corner. In other words, the first humid gas inlet 123 and the first humid gas outlet 125 are formed at the corners of the concave groove 121 oppositely. By doing so, the humid gas supplied from the first humid gas inlet 123 is moved along the plurality of channels 140 formed at the bottom surface of the concave groove 121 and then discharged at the first humid gas outlet 125.

In addition, the channels 140 of this embodiment are formed at the bottom surface of the concave groove 121 side by side in a concavely depressed form with an open top. Also, the channels 140 allow the first humid gas inlet 123 and the first humid gas outlet 125 to communicate with each other.

In addition, in this embodiment, the plurality of channels 140 are arranged side by side in a zigzag form at the bottom surface of the concave groove 121.

As shown in FIG. 5, since the plurality of channels 140 are formed in a zigzag form from the top of the concave groove 121 to the bottom thereof, the humid gas flows in a right horizontal direction along the plurality of channels 140 from an upper left corner of the concave groove 121 having the first humid gas inlet 123, continuously flows downwards, moves in a left horizontal direction again, and then continuously moves downwards. After repeating this process, the humid gas is discharged through the first humid gas outlet 125.

As described above, the humid gas is moved along the plurality of channels 140 and then discharged through the first humid gas outlet 125 formed in the lower right corner of the concave groove 121.

Meanwhile, in this embodiment, the gas distribution unit 150 is detachably connected to the concave groove 121 to uniformly discharge the humid gas toward the electrolytic membrane M, so that the humid gas moving along the plurality of channels 140 is uniformly distributed toward the electrolytic membrane M.

Since a homogeneous humid gas atmosphere is formed inside the humidification chamber 110 by means of the gas distribution unit 150, it is possible in to uniformly measure the hydrogen ion conductivity over the entire region of the electrolytic membrane M accommodated in the humidification chamber 110.

Referring to FIGS. 4 to 6, the gas distribution unit 150 includes a gas distribution plate 150 inserted into the concave groove 121 formed in the chamber block 120 to be closely adhered to a top portion of the plurality of channels 140 and having a plurality of gas distribution holes 151 formed to communicate with the plurality of channels 140.

In this embodiment, since the channel 140 is formed in a concavely depressed form with an open top, when the gas distribution plate 150 is inserted into the concave groove 121 and closely adhered to the open top of the open channel 140, the top portion of the channel 140 to which the gas distribution plate 150 is closely adhered is sealed.

Thus, due to the pressure of the humid gas supplied from the first humid gas inlet 123, the humid gas flows along the plurality of channels 140 toward the first humid gas outlet 125. In addition, if the plurality of gas distribution holes 151 formed in the gas distribution plate 150 are located at the top portion of the channels 140, the humid gas flowing along the channels 140 is discharged toward the electrolytic membrane M through the gas distribution holes 151.

In this embodiment, the gas distribution hole 151 of the gas distribution plate 150 is formed to have a diameter greater than a width of the channel 140, so that the humid gas may be easily discharged from the channel 140 to the gas distribution hole 151.

In this embodiment, since the plurality of gas distribution holes 151 are formed in the gas distribution plate 150 and are uniformly arranged to be spaced apart from each other by a predetermined distance, the humid gas may be uniformly discharged toward the electrolytic membrane M through the gas distribution holes 151. Thus, the ionic conductivity may be uniformly measured over the entire region of the electrolytic membrane M accommodated in the humidification chamber 110.

In addition, since the pressure and temperature conditions are identically formed throughout the entire region of the humidification chamber 110 by the gas distribution plate 150 having the plurality of gas distribution holes 151 and the plurality of channels 140, while the ionic conductivity of the electrolytic membrane M is being measured in the humidification chamber 110, it is possible to prevent water from condensing in the humidification chamber 110 and accumulating in the humidification chamber 110.

In this embodiment, the chamber block 120 and the gas distribution plate 150 may be made of any one of polyetherether ketone (PEEK) and polytetrafluoro ethylene (PTFE), which are electrically insulated and thermally, chemically and mechanically stabilized.

Meanwhile, referring to FIG. 4, when the gas distribution plate 150 is inserted into the concave groove 121 of the chamber block 120, the plurality of electrodes 160 are closely adhered to the gas distribution plate 150 and supported thereby. In this embodiment, the electrodes 160 may employ a platinum (Pt) electrode.

The plurality of electrodes 160 are provided to measure the uniformity of the ionic conductivity over the entire region of the electrolytic membrane M, and the plurality of electrodes 160 are arranged side by side so that one side of the electrolytic membrane M is in contact with the plurality of electrodes 160.

The ionic conductivity indicates the degree of hydrogen ion exchange capability of the electrolytic membrane M. The electrolytic membrane M should have high ionic conductivity, and the ionic conductivity should be uniform over the entire region. The ionic conductivity of the electrolytic membrane M may be figured out by measuring an impedance of the electrolytic membrane M by means of the plurality of electrodes 160.

In other words, the ionic conductivity ($\sigma$) of the electrolytic membrane M may be obtained using Equation (1) below.

$$\sigma = \frac{L}{RDW} \quad \text{Equation (1)}$$

Here, L is a distance between the electrodes 160, R is an impedance of the electrolytic membrane M, D is a thickness of the electrolytic membrane M, and W is a width of the electrolytic membrane M.

In addition, referring to FIGS. 2 to 4, the ionic conductivity measurement device 100 of an electrolytic membrane according to an embodiment of the present disclosure further includes a sealing member 170 disposed at an outer side of the pair of concave grooves 121 to seal the measurement space formed between the pair of chamber blocks 120 when the pair of chamber blocks are coupled to be closely adhered to each other.

In this embodiment, the sealing member 170 may be made of various materials, such as rubber and Teflon, as long as the measurement space may be sealed.

In this embodiment, the sealing member 170 is disposed to surround the outer side of the concave groove 121 formed in each chamber block 120 to prevent the humid gas from leaking to the outside due to the plurality of electrodes 160 crossing the top portion of the concave groove 121 when the pair of the chamber blocks 120 are closely adhered and coupled to each other.

In addition, the ionic conductivity measurement device 100 of an electrolytic membrane according to an embodiment of the present disclosure may further include a temperature adjustment unit 180 installed at the humidification chamber 110 to adjust an internal temperature of the measurement space, so that the ionic conductivity of the electrolytic membrane M may be measured while changing the temperature in the humidification chamber 110.

The temperature adjustment unit 180 of this embodiment includes a heat bar 180 inserted into one of the pair of chamber blocks 120 of the humidification chamber 110 to heat the humidification chamber 110. The heat bar 180 may be connected to a separate power source to control the temperature of the humidification chamber 110 by controlling the power.

At this time, the ionic conductivity measurement device 100 of an electrolytic membrane according to an embodiment of the present disclosure may further include a temperature sensor 190 for measuring the temperature of the measurement space in the humidification chamber 110 by the heat bar 180. The temperature sensor 190 is inserted into a temperature sensor insert groove 127 formed at one side of the chamber block 120 to measure the temperature of the measurement space.

In addition, the ionic conductivity measurement device 100 of an electrolytic membrane according to an embodiment of the present disclosure may further include a pair of end blocks 130 coupled to the outer side of the pair of chamber blocks 120, respectively.

Also, a second humid gas inlet 131 and a second humid gas outlet 133 are formed in the end block 130 to communicate with the first humid gas inlet 123 and the first humid gas outlet 125, respectively.

In addition, when the pair of end blocks 130 are provided at the outer side of the pair of chamber blocks 120, the heat bar 180 is inserted into the heat bar insert groove 135 formed at the end block 130 to directly heat the end block 130 and indirectly heat the chamber block 120 and the measurement space. In this embodiment, the end block 130 may be made of a metal such as aluminum to improve the thermal conductivity by the heat bar 180.

Hereinafter, the operation of the ionic conductivity measurement device 100 of an electrolytic membrane according to the present disclosure will be described.

First, in order to measure the ionic conductivity of the electrolytic membrane M, as shown in FIG. 4, the gas distribution plate 150 is inserted into the concave groove 121 formed at the chamber block 120, and the plurality of electrodes 160 are installed side by side to be spaced apart from each other by a predetermined distance so as to be closely adhered to the gas distribution plate 150. In addition, the electrolytic membrane M is disposed over the plurality of electrodes 160.

In addition, the pair of chamber blocks 120 are closely adhered and coupled to each other to be sealed with the electrolytic membrane M being interposed therebetween.

Also, as shown in FIG. 1, in a state where the pair of end blocks 130 are respectively installed at the pair of chamber blocks 120, and a humid gas supply line L1 and a humid gas discharge line L2 are respectively connected to the second humid gas inlet 131 and the second humid gas outlet 133 formed at the pair of end blocks 130 so that the humid gas is supplied to and discharged from the humidification chamber 110.

In addition, the ionic conductivity of the electrolytic membrane M may be measured while changing the temperature inside the humidification chamber 110 by adjusting the heating temperature of the heat bar 180 installed at the end block 130.

The present disclosure is not limited to the above embodiments but may be changed or modified in various ways without departing from the features and scope of the present disclosure, as apparent to those skilled in the art. Therefore, such modifications or variations are intended to fall within the scope of the claims of the present disclosure.

[Reference Signs]

| | |
|---|---|
| 100: ionic conductivity measurement device of an electrolytic membrane | |
| 110: humidification chamber | |
| 120: chamber block | 121: concave groove |
| 123: first humid gas inlet | 125: first humid gas outlet |
| 127: temperature sensor insert groove | 130: end block |
| 131: second humid gas inlet | 133: second humid gas outlet |
| 135: heat bar insert groove | 140: channel |
| 150: gas distribution unit | 151: gas distribution hole |
| 160: electrode | 170: sealing member |
| 180: temperature adjustment unit | 190: temperature sensor |

What is claimed is:

1. An ionic conductivity measurement device of an electrolytic membrane, comprising:

a humidification chamber configured to accommodate an ion-conductive electrolytic membrane and having concave grooves respectively formed at both sides thereof which face the electrolytic membrane to form a measurement space for measuring ionic conductivity of the electrolytic membrane, the humidification chamber having a first humid gas inlet and a first humid gas outlet formed through the concave groove;

a plurality of channels formed at a bottom surface of each of the concave grooves so that the first humid gas inlet and the first humid gas outlet are connected to communicate with each other, the plurality of channels having an open top;

a gas distribution unit detachably coupled to each of the concave grooves with the electrolytic membrane being interposed therebetween, the gas distribution unit being closely adhered to a top portion of the plurality of channels and uniformly distributing the humid gas moving along the plurality of channels toward the electrolytic membrane; and a plurality of electrodes provided in contact with one side of the electrolytic membrane and supported by the gas distribution unit, the plurality of electrodes being disposed side by side to measure an impedance of the electrolytic membrane.

2. The ionic conductivity measurement device of an electrolytic membrane according to claim 1, wherein the first humid gas inlet and the first humid gas outlet are formed at edges of the concave grooves oppositely, and wherein the plurality of channels are formed at the bottom surface of the concave groove in a concavely depressed form with an open top and are arranged side by side.

3. The ionic conductivity measurement device of an electrolytic membrane according to claim 2, wherein the plurality of channels are disposed at the bottom surface of the concave groove side by side in a zigzag form.

4. The ionic conductivity measurement device of an electrolytic membrane according to claim 2, wherein the gas distribution unit includes a gas distribution plate inserted into the concave groove and closely adhered to the top of the plurality of channels and having a plurality of gas distribution holes communicating with the plurality of channels.

5. The ionic conductivity measurement device of an electrolytic membrane according to claim 4, wherein the gas distribution hole is formed to have a diameter greater than a width of the channel.

6. The ionic conductivity measurement device of an electrolytic membrane according to claim 1, wherein the humidification chamber includes a pair of chamber blocks so that the concave groove is formed at one surface thereof which faces the electrolytic membrane, the pair of chamber blocks are coupled to be closely adhered to each other to form the measurement space, and the first humid gas inlet and the first humid gas outlet are formed in the pair of chamber blocks through the concave groove.

7. The ionic conductivity measurement device of an electrolytic membrane according to claim 6, further comprising:

a temperature sensor inserted into one side of the chamber block to measure temperature of the measurement space.

8. The ionic conductivity measurement device of an electrolytic membrane according to claim 6, further comprising:

a sealing member disposed to surround an outer side of the concave groove to seal the pair of chamber blocks to each other when the pair of chamber blocks are coupled to be closely adhered to each other.

9. The ionic conductivity measurement device of an electrolytic membrane according to claim 6, further comprising:

a temperature adjustment unit installed at the humidification chamber to adjust internal temperature of the measurement space.

10. The ionic conductivity measurement device of an electrolytic membrane according to claim 9, wherein the humidification chamber further includes a pair of end blocks respectively coupled to outer sides of the pair of chamber blocks and having a second humid gas inlet and a second humid gas outlet formed to communicate with the first humid gas inlet and the first humid gas outlet, respectively, and wherein the temperature adjustment unit includes a heat bar inserted into one side of the end block to adjust internal temperature of the measurement space.

11. The ionic conductivity measurement device of an electrolytic membrane according to claim 6, wherein the chamber block and the gas distribution unit are made of any one of polyetherether ketone (PEEK) and polytetrafluoro ethylene (PTFE).

* * * * *